Figure 1:
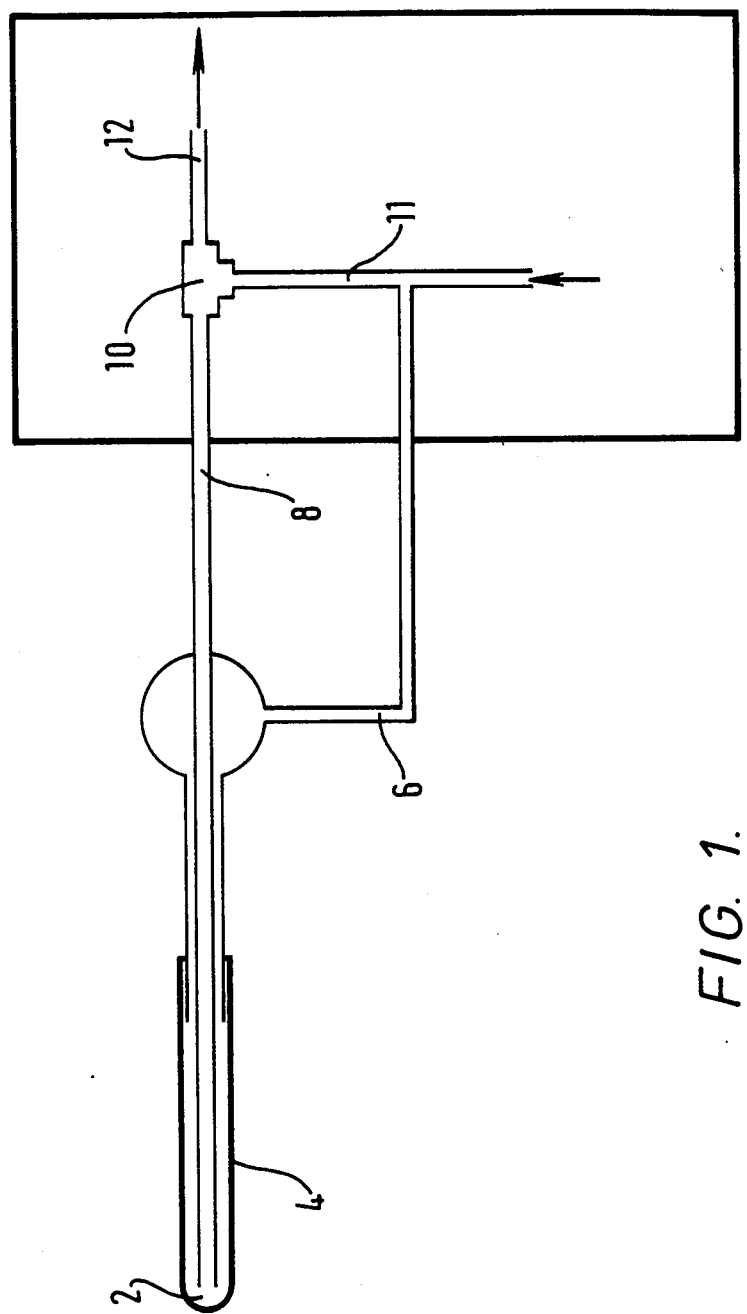

United States Patent [19]

Jumeau

[11] Patent Number: 4,706,700
[45] Date of Patent: Nov. 17, 1987

[54] VALVE ARRANGEMENT

[75] Inventor: Elizabeth J. Jumeau, Liverpool, England

[73] Assignee: The BOC Group, Inc., Montvale, N.J.

[21] Appl. No.: 907,932

[22] Filed: Sep. 16, 1986

[30] Foreign Application Priority Data

Oct. 30, 1985 [GB] United Kingdom ............... 8526758

[51] Int. Cl.$^4$ ............................................. F16K 13/10
[52] U.S. Cl. ............................. 137/247.29; 137/602; 73/23.1
[58] Field of Search ............... 137/247.29, 599.1, 602; 73/23.1

[56]         References Cited
        U.S. PATENT DOCUMENTS

| 3,186,808 | 6/1965 | Anscherlik | 137/602 X |
| 3,738,107 | 6/1973 | Miller | 137/602 X |
| 4,168,724 | 9/1979 | Graffunder et al. | 137/606 |
| 4,281,935 | 8/1981 | Cramer et al. | 366/174 |

FOREIGN PATENT DOCUMENTS

| 1478855 | 4/1967 | France | 137/602 |
| 800212 | 8/1958 | United Kingdom . | |
| 1480010 | 7/1977 | United Kingdom . | |
| 2017907A | 10/1979 | United Kingdom . | |

Primary Examiner—A. Michael Chambers
Assistant Examiner—John C. Fox
Attorney, Agent, or Firm—Roger M. Rathbun; Larry R. Cassett

[57]         ABSTRACT

A valve arrangement for controlling the flow of a sample of blood gases along a capillaric streamway from a probe towards an analyzing apparatus includes a body 12 having an inlet 36 for control fluid and a reciprocable valve head 20 movable from a first position in which inlet 36 is isolated from a second inlet 30 for carrier gas and blood gases towards a second position in which inlets 36, 30 are in communication. The arrangement is such, that in the first position of the valve head 20 the carrier gas and blood gases can flow from inlet 30 towards an outlet 32. However, in the second position the pressure of the control fluid prevents the flow of the carrier gas and blood gases through the inlet 30.

5 Claims, 2 Drawing Figures

VALVE ARRANGEMENT

The present invention relates to valve arrangements and in particular to valve arrangements for controlling the flow of gas in micro-bore capillary tubes and having a minimum of "dead space". The present invention is particularly concerned with the control of sample gas moving in a carrier gas stream, as in gas chromatography, gas chromatography-mass spectrometry and mass spectrometry.

It is known, for the measurement and analysis of blood gases in vivo, to use an intravascular probe. One end of the probe is inserted into a vein or artery whilst the other is connected to an analyser. Gases absorbed in the blood diffuse through a membrane forming part of the probe and move, towards the analyser, as a bolus in an inert carrier gas such as helium. A valve controls in an on/off manner the flow of carrier gas and the bolus of blood gases from the probe towards the analyser.

It is an aim of the present invention to provide a valve arrangement in which there is a minimum of "dead space" with the object of minimising the likelihood of distortion of the bolus of blood gases and which therefore makes it suitable for controlling the flow of carrier gas and a minute bolus of sample gases from a probe, or other source of sample gas, towards an analyser.

According to the present invention, a valve arrangement comprises a body having a first inlet for a first control fluid, a member movable from a first position in which the first inlet is isolated from a second inlet for a second fluid the flow of which is to be controlled and a second position in which the first and second inlets are in communication, the arrangement being such that in the first position of said member the second fluid can flow from the second inlet towards an outlet spaced therefrom but when said member is in the second position the pressure of the first control fluid prevents the flow of the second fluid from the second inlet towards the outlet.

Figure 2:
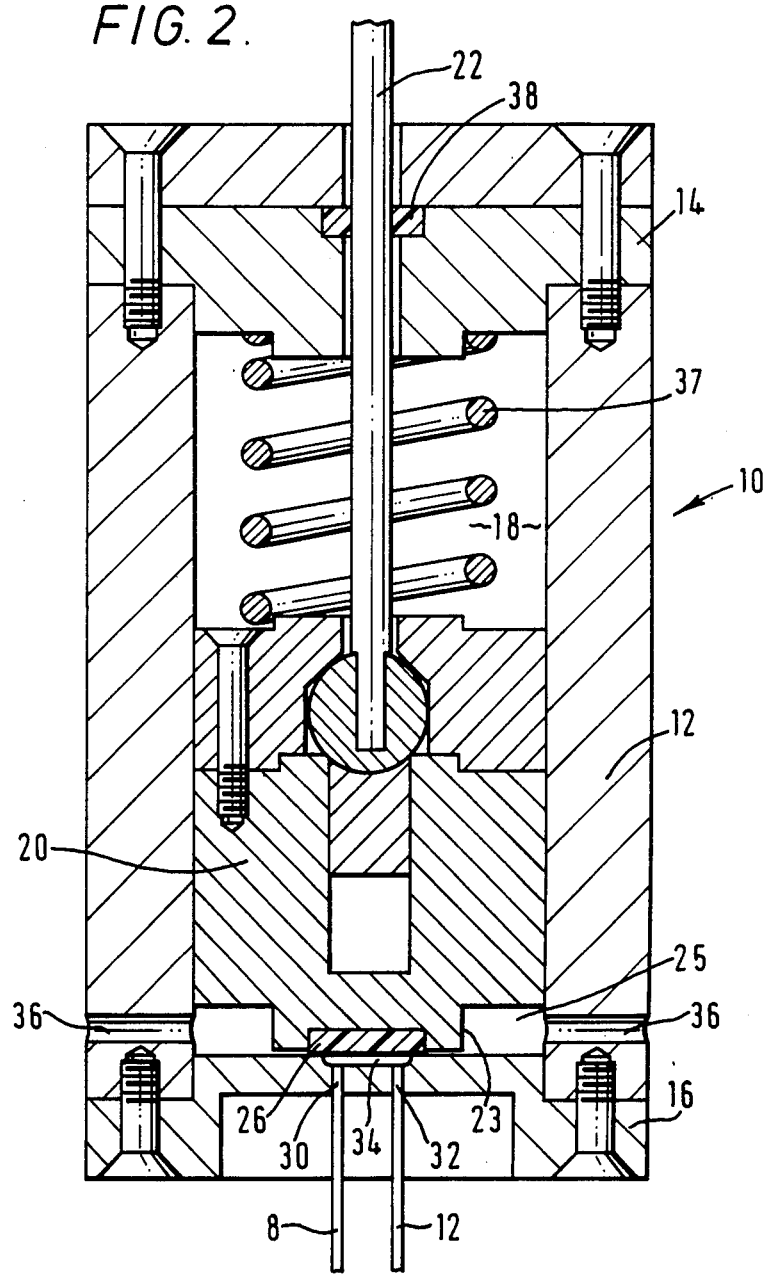

An embodiment of the invention will now be described by way of example, reference being made to the Figures of the accompanying diagrammatic drawings, in which:

FIG. 1 is a schematic diagram illustrating a gas network for an intravascular probe for use in the analysis of blood gases; and FIG. 2 is a sectional view through a valve arrangement for controlling the flow of gases from the probe of FIG. 1 to an analyser.

As shown with reference to FIG. 1, a probe 2 for insertion into a vein or artery of a patient has an outer membrane 4 through which blood gases can diffuse. An inert carrier gas, for example helium, is pumped under pressure from a source (not shown) through a passageway 6 into the interior of the probe 2 and the carrier gas, together with a bolus of blood gases, leaves the probe via a passageway 8 towards a valve assembly 10. The valve assembly 10 is positioned between the probe 2 and an analyser (not shown) and a passageway 12 extends from the valve assembly 10 towards the analyser.

A proportion of the carrier gas from the source is directed via passageway 11 to the valve assembly 10 and acts as a "control fluid" in a manner to be described.

Referring also to FIG. 2, the valve assembly 10 includes a central body 12 and end walls 14, 16 which between them define a space 18 which accommodates a member in the form of a valve head 20. Attached to the valve head 20 is a valve stem 22 which passes through a grommet seal 38 in the end wall 14. At its outer end the valve stem 22 may have attached, a solenoid actuator or a screw thread device (not shown). It will be evident, that by actuating the solenoid, the valve head 20 will be caused to move away from the end wall 16 within the space 18 such that a spring 37 is compressed. When the solenoid is de-activated the valve head 20 will be caused to move towards, and be held in contact with, the end wall 16 by the tension of the compression spring 37. A similar action can obtain by means of a screwthread device.

The valve head 20 is formed immediately adjacent the end wall 16 with a central boss 23 which is counterbored to receive a seal 26 made from VITON. The boss 23 defines with a surface of the central body 12 an annular space 25 which communicates with inlet(s) 36 connected to the passageway 11 from the carrier gas source.

The end wall 16 is formed with an inlet bore 30 and spaced therefrom an outlet bore 32 which connect respectively with the passageways 8 and 12. Between the inlet bore and the outlet bore there is formed a shallow channel 34.

By way of example, the inlet and outlet bore diameters can be of the order of 150 micron diameter and their centre distances can be 300 micron apart. The width of the channel 34 will also be 150 micron and its depth 50 micron. Such dimensioning will give a dead space for the valve assembly of less than 0.003 micro liters.

In use, with the valve assembly 10 open, the valve head 20 will occupy a first position as shown in FIG. 2. The carrier gas will leave the probe 2, pass along the passageway 8 into the inlet bore 30 along the channel 34 and hence out from the outlet bore 32 and into the passageway 12 towards the analyser. The seal 26 engages resiliently the surface of the end wall 16 thereby isolating the inlet(s) 36 from the inlet bore 30, channel 34 and outlet bore 32.

When it is desired to stop the flow of carrier gas and blood gas from the probe 2 to the analyser, the solenoid is actuated, causing the valve head 20 to move away from the end wall 16 which will permit the inert carrier gas under pressure to flow via inlets 36 into space 25 and communicate with the inlet bore 30. The pressure of the inert gas which acts as a control gas balances the pressure of the gases in the probe and thereby prevents the flow of blood gas and carrier gas from the inlet bore 30 into the outlet bore 32.

Furthermore, any suction created by the analyser in the outlet bore 32 will take preferentially the carrier gas occupying the space 25.

In the above described embodiment, the dead space, i.e. the volume of the channel 34, is sufficiently small that it will not affect adversely the bolus of blood gas being carried by the carrier gas towards the analyser.

The embodiment described above is particularly effective for controlling the flow of a sample of blood gases along a capillaric streamway from a probe towards an analysing apparatus, such as a mass spectrometer.

What is claimed is:

1. A valve arrangement comprising a body having a first inlet for a first control fluid, said body including a first end wall formed with two spaced bores defining respectively a second inlet for a second fluid the flow of which is to be controlled and an outlet for said second fluid, a shallow channel extending between the second inlet and said outlet for the flow of the second fluid, and a member movable from a first position in which said first inlet is isolated from said second inlet and a second position in which said first and second inlets are in communication, the arrangement being such that in the first position of said member the second fluid can flow from said second inlet towards said outlet but when said member is in the second position the pressure of the first control fluid prevents the flow of the second fluid from the second inlet towards said outlet.

2. A valve arrangement as claimed in claim 1, in which the volume of the channel is not greater than 0.003 micro liters.

3. A valve arrangement as claimed in any one of claim 1, in which the movable member has a resilient surface immediately adjacent the channel thereby to isolate the second inlet, channel and outlet from the first inlet in the first position of the movable member.

4. A valve arrangement as claimed in claim 3, in which the movable member is biased towards its first position by means of a compression spring.

5. A valve arrangement as claimed in any one of claims 2 or 3 in which the movable member includes a valve head and a valve stem connected thereto, the valve stem passing through a grommet seal in a second end wall of the body such that by energising a solenoid or screw thread device attached to the valve stem, the valve head is caused to reciprocate within the body towards and away from the first end wall.

* * * * *